(12) United States Patent
Watanabe et al.

(10) Patent No.: US 6,303,013 B1
(45) Date of Patent: Oct. 16, 2001

(54) GAS SENSOR INCLUDING CAULKED FIXATION PORTION FOR FIXING DETECTION ELEMENT BY CAULKING

(75) Inventors: Isao Watanabe, Nagoya; Takashi Kojima, Kasugai, both of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/476,113

(22) Filed: Jan. 3, 2000

(30) Foreign Application Priority Data

Jan. 8, 1999 (JP) .................................................. 11-00312
Nov. 30, 1999 (JP) ................................................ 11-340286

(51) Int. Cl.$^7$ .................................................. G01N 27/407
(52) U.S. Cl. .................. 204/428; 204/279; 204/297.01; 29/592.1; 29/595
(58) Field of Search .................... 204/421–429, 204/279, 297.01; 73/31.05, 23.31, 23.32; 29/761, 592.1, 595

(56) References Cited

U.S. PATENT DOCUMENTS

| | | | |
|---|---|---|---|
| 4,705,915 | * 11/1987 | Van Brunt et al. | 174/35 R |
| 5,135,264 | * 8/1992 | Elliot-Moore | 285/2 |
| 5,830,339 | * 11/1998 | Watanabe et al. | 204/426 |
| 5,859,361 | * 1/1999 | Fukaya et al. | 73/23.32 |
| 5,874,663 | * 2/1999 | Fukaya et al. | 73/23.32 |

FOREIGN PATENT DOCUMENTS 2-147817  6/1990  (JP) .
8-160002  6/1996  (JP) .

* cited by examiner

Primary Examiner—Robert J. Warden, Sr.
Assistant Examiner—Kaj K. Olsen
(74) Attorney, Agent, or Firm—Pillsbury Winthrop LLP (57) ABSTRACT

A gas sensor has a housing integrally formed with a caulked fixation portion. A detection element is inserted into the housing and fixed therein by caulking the caulked fixation portion via a sealing member such as a metallic ring. The caulked fixation portion is composed of a caulked portion and a buckling portion, and satisfies dimensional relationships of $T1<T3<T2$; $2<T2/T1$, and $3<L/\{(T1+T2)/2\}$. T1 is a minimum thickness of the caulked portion, and T2 is a maximum thickness of the caulked portion. T3 is an average thickness of the buckling portion, and L is a length of the caulked portion in an axial direction of the gas sensor.

16 Claims, 6 Drawing Sheets

GAS SENSOR INCLUDING CAULKED FIXATION PORTION FOR FIXING DETECTION ELEMENT BY CAULKING

CROSS REFERENCE TO RELATED APPLICATIONS

This application is based upon and claims the benefit of Japanese Patent Application No. 11-3312 filed on Jan. 8, 1999, and No. 11-340286 filed on Nov. 30, 1999, the contents of which are incorporated herein by reference.

BACKGROUND OF THE INVENTION

1. Field of the Invention

This invention relates to a gas sensor installed in an exhaust system of an automotive internal combustion engine for measuring a specific gas concentration in exhaust gas or the like.

2. Description of the Related Art

A gas sensor installed in an exhaust system such as an exhaust manifold or an exhaust gas pipe of an automotive combustion engine is required to have durability to harsh environment such as high temperature and hard vibration. Parts for making up the gas sensor are therefore fixed to one another by caulking and welding, because fastening with screws is insufficient to fix the parts.

The caulking fixation is processing accompanied by plastic deformation. It is known that when a processing load (caulking load) is relieved after the caulking fixation is performed, a spring-back action readily occurs to prevent a caulked fixation portion, which is fixed by caulking, from having a sufficient fastening strength. Therefore, in the caulking fixation, hot-caulking is performed after performing cold-caulking.

Figure 8:
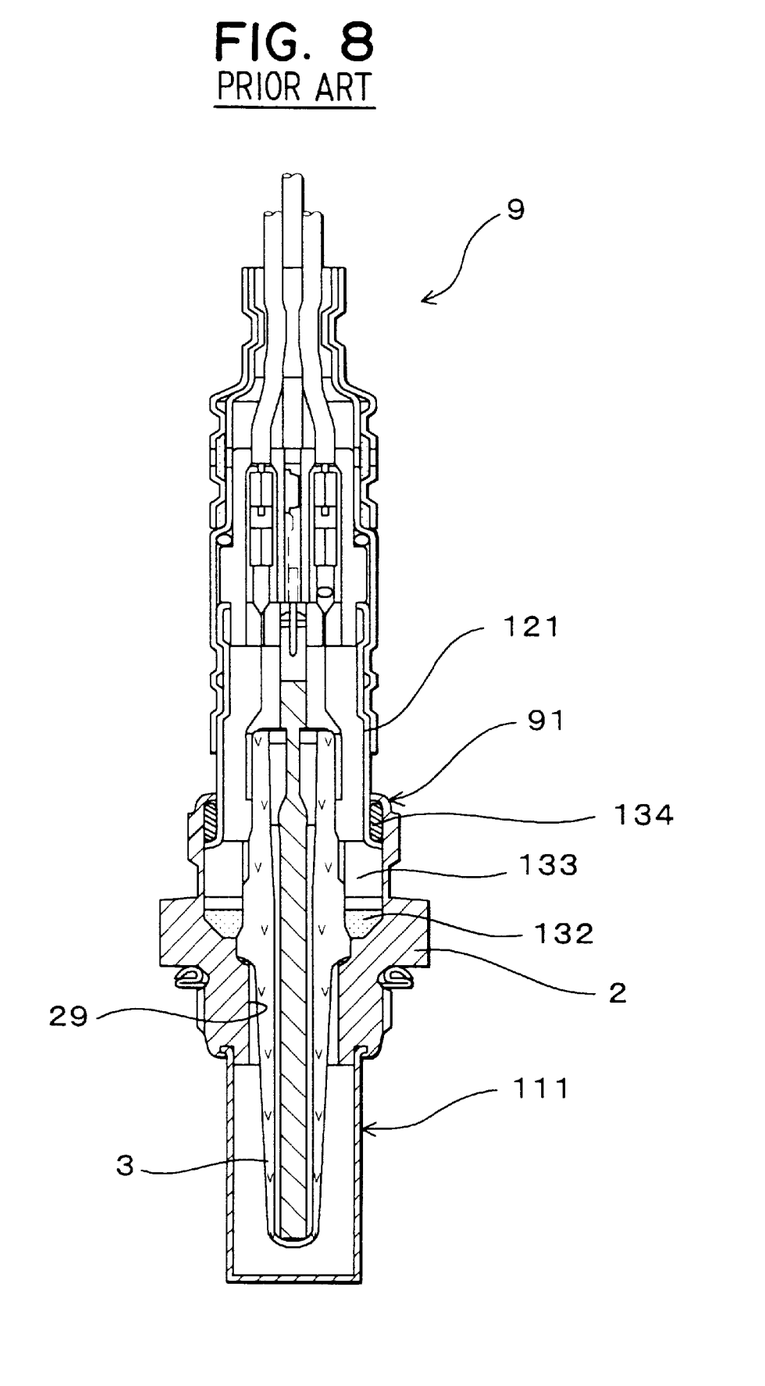
FIG. 8 is a cross-sectional view showing a gas sensor in a prior art.

FIG. 8 shows a typical structure of a gas sensor 9. The gas sensor 9 is composed of a housing 2 having an insertion hole 29 into which a detection element 3 is inserted, a measurement gas side cover 111 fixed to an end portion of the housing 2, and an air side cover 121 fixed to the other end portion of the housing 2. A space defined by the detection element 3 in the insertion hole 29 is filled with powdery sealing material 132. The powdery sealing material 132 is pushed by a metallic ring 134, which is fixed to a caulked fixation portion 91 by caulking, through an insulating member 133, and the like. In the caulking fixation, specifically, the caulked fixation portion 91 is bent by caulking to hold the metallic ring 134, thereby fixing the metallic ring 134.

Figure 9:
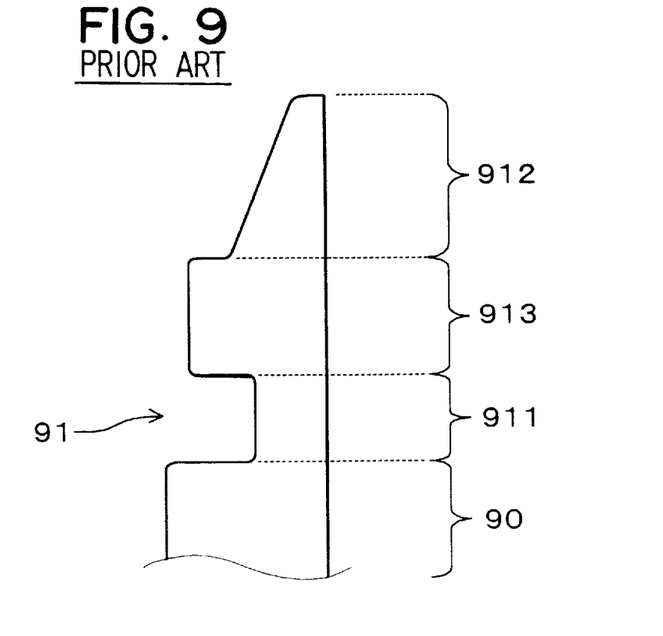
FIG. 9 is a schematic view showing a caulked fixation portion in the prior art.

FIG. 9 shows the caulked fixation portion 91 before it is caulked. The caulked fixation portion 91 is integrally formed with a body portion 90 of the housing 2, and is composed of a buckling portion 911, a thick portion 913, and a caulked portion 912 provided in this order from the housing body portion 90. The caulked fixation portion 91 is caulked by cold-caulking and hot-caulking as described above, so that the detection element 3 is fixed by pressure via the metallic ring 134, the insulating member 133, and the powdery sealing material 132.

The thick portion 913 of the caulked fixation portion 91 is provided so that the deformation of the caulked portion is securely performed by caulking and so that the buckling portion is easily buckled. However, the thick portion 913 increases the weight of the housing 2, and increases the size of the gas sensor 9. The increases in size and weight are opposed to recent requirements to parts for the engine. To comply with strengthened exhaust gas regulations, every part for the engine is required to have a reduced size and a reduced weight to thereby reduce a load to the engine. The caulked fixation portion is therefore required to have a structure capable of securely performing the caulking fixation without having the thick portion. Lightening the gas sensor can additionally produce a material cost reduction.

SUMMARY OF THE INVENTION

The present invention has been made in view of the above limitations. An object of the present invention is to provide a gas sensor with a reduced size and a reduced weight, at a low material cost.

According to the present invention, a gas sensor has a caulked fixation portion integrated with a housing, for fixing a detection element in an insertion hole of the housing, by caulking. The caulked fixation portion has a caulked portion for imparting a caulking force to a sealing member directly, and a buckling portion provided at a housing side of the caulked portion for increasing the caulking force by buckling in an axial direction of the housing.

The caulked fixation portion before caulked satisfies dimensional relationships of $T1<T3<T2$; $2<T2/T1$; and $3<L/\{(T1+T2)/2\}$. $T1$ is a minimum thickness of the caulked portion in a radial direction of the housing, and $T2$ is a maximum thickness of the caulked portion in the radial direction. $T3$ is an average thickness of the buckling portion in the radial direction, and $L$ is a length of the caulked portion in the axial direction. The caulked fixation portion does not have a thick portion.

Accordingly, the gas sensor of the present invention can be provided with a reduced size and a reduced weight of the housing at low material cost. Because the caulked fixation portion before caulked satisfies the dimensional relationships described above, S-like buckling is not produced at the caulked fixation portion. Therefore, a cover can securely fixed to the housing. This also contributes the size reduction of the gas sensor.

BRIEF DESCRIPTION OF THE DRAWINGS

Other objects and features of the present invention will become more readily apparent from a better understanding of the preferred embodiments described below with reference to the following drawings, in which.

DETAILED DESCRIPTION OF THE PREFERRED EMBODIMENT

A gas sensor 1 according to a preferred embodiment of the present invention is explained with reference to FIGS. 1 through 6, in which the same parts as those shown in FIG. 8 are indicated by the same reference numerals. The gas sensor 1 is an oxygen sensor, which is installed in an exhaust system of an automotive internal combustion engine to control combustion of the combustion engine.

Figure 2:
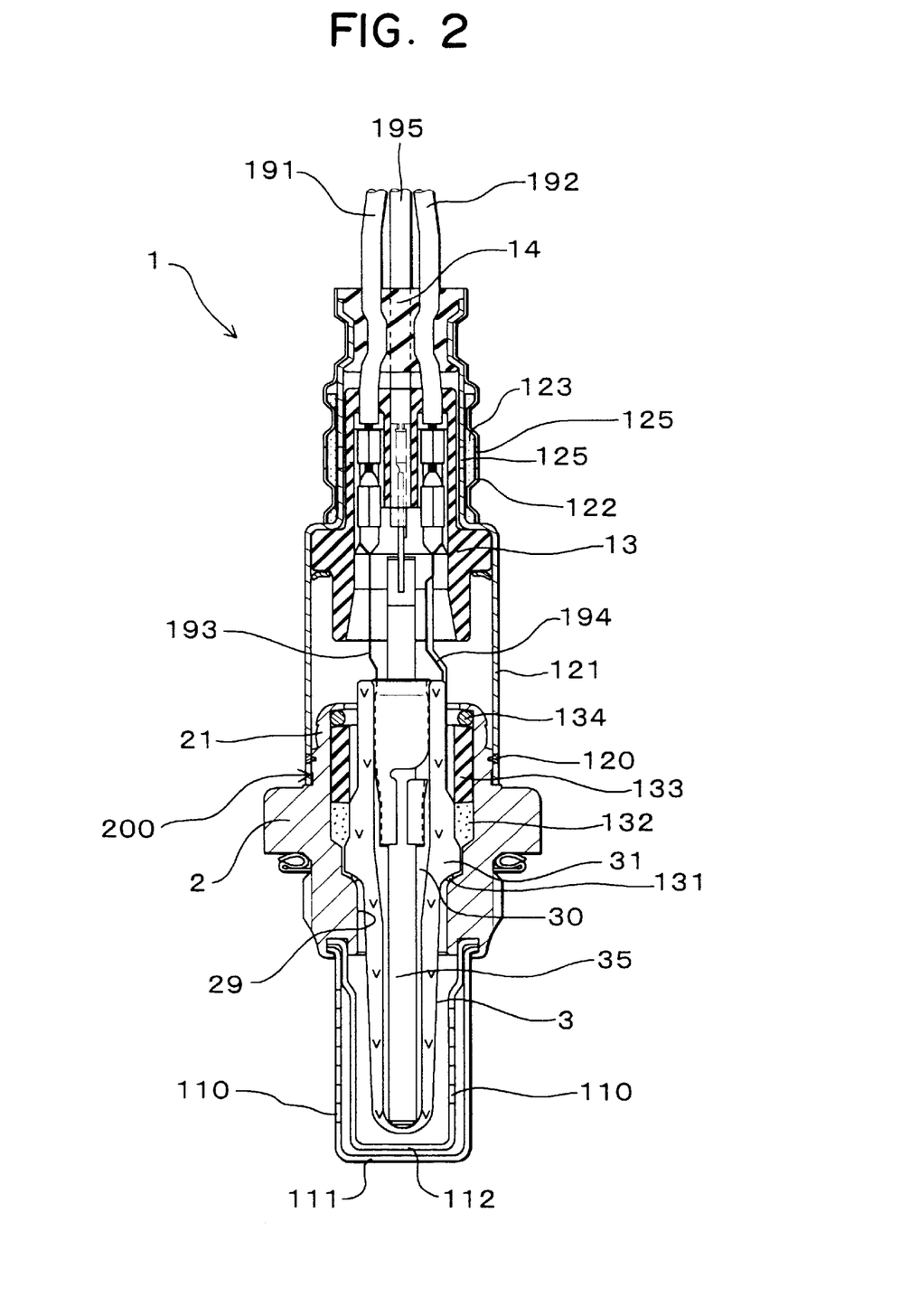
FIG. 2 is a cross-sectional view showing the gas sensor in the embodiment.

As shown in FIG. 2, the gas sensor 1 is composed of a cylindrical housing 2 having an insertion hole 29, a measurement gas side double cover 111, 112 covering an end portion of the housing 2, and an air side cover 121, which is fixed to an outer circumference wall 200 at an fixed portion 120 of the housing 2 by welding for covering the other end portion of the housing 2. The housing 2 has a caulked fixation portion 21 at a portion upper than the fixed portion 120 of the air side cover 121.

Figure 3:
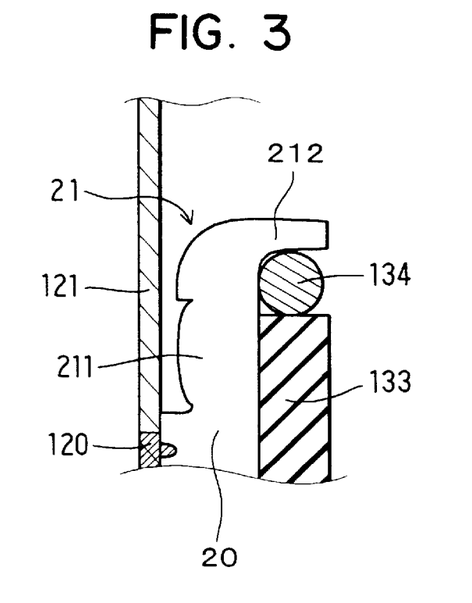
FIG. 3 is a schematic view showing the caulked fixation portion after caulked.

As shown in FIGS. 2 and 3, a detection element 3 is disposed in the insertion hole 29 through a sealing member 131 and is fixed to the housing 2 by caulking via a metallic ring 134. A space defined by the detection element 3 in the insertion hole 29 is filled with powdery sealing material 132 such as talc, and the sealing material 132 is pushed by the metallic ring 134 through an insulating member 133.

Figure 5A:
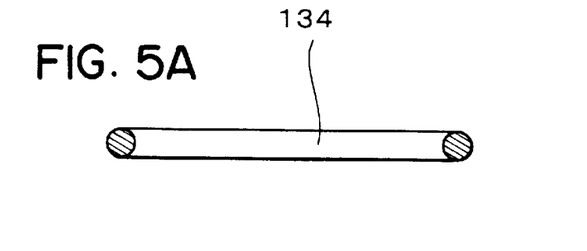
FIG. 5A is a cross-sectional view showing a metallic ring of the gas sensor in the embodiment.
Figure 5B:
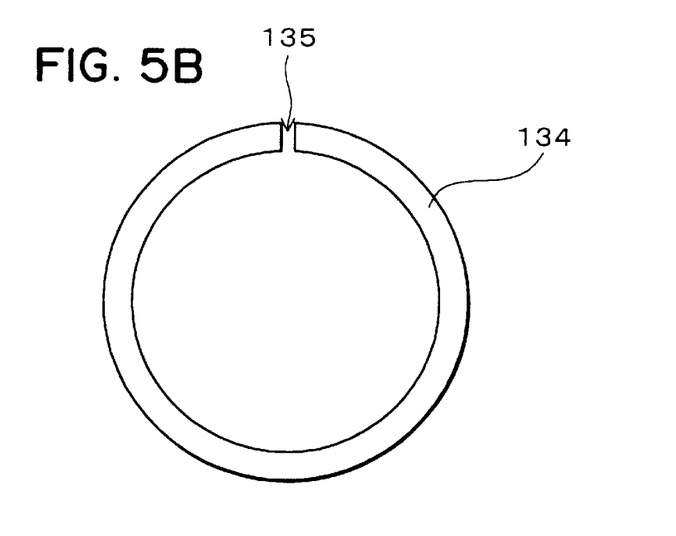
FIG. 5B is a plan view showing the metallic ring.

An inside of the air side cover 121 and an inside of the measurement gas side cover 112 are air-tightly divided from each other by the sealing member 131, the powdery sealing material 132, and the like to prevent gas communication therebetween. The metallic ring 134 is, as shown in FIGS. 5A and 5B, 12.9 mm in outer diameter having a notch 135 (width: approximately 0.5 mm). The notch 135 has a circular shape in cross-section with a diameter of approximately 1 mm. The metallic ring 134 can be easily assembled, and easily manufactured due to the notch 135 thereof.

Figure 1:
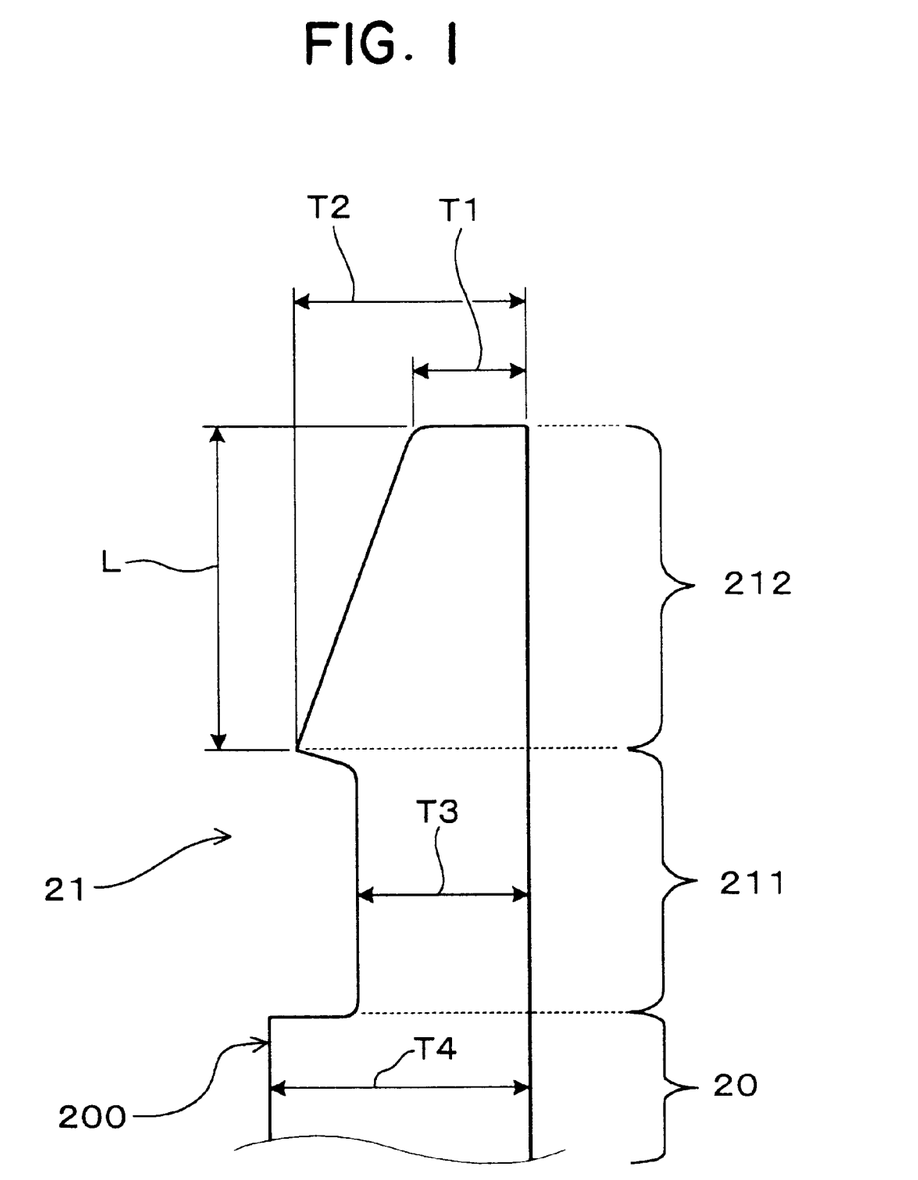
FIG. 1 is a schematic view showing a caulked fixation portion of a gas sensor before caulked in a preferred embodiment according to the present invention.

As shown in FIG. 1, the caulked fixation portion 21 of the housing 2 includes a caulked portion 212 for applying a caulking force to the metallic ring 134 directly, a buckling portion 211 provided at a housing side of the caulked portion 212 for increasing the caulking force derived from the caulked portion 212 by buckling. The caulked fixation portion 21 satisfies following dimensional relationships (1) to (3) before fixing the detection element 3 in the insertion hole 29 by caulking;

$$T1 < T3 < T2 \quad (1)$$

$$2 < T2/T1 \quad (2)$$

$$3 < L/\{(T1+T2)/2\} \quad (3)$$

in which T1 represents a minimum thickness of the caulked portion 212, T2 is a maximum thickness of the caulked portion 212, T3 is an average thickness of the buckling portion 211, and L is a length of the caulked portion 212 in a gas sensor axial direction.

The caulked portion 212 has the minimum thickness T1 at a front end thereof, and the maximum thickness T2 at the other end on the buckling portion side. The buckling portion 211 has a generally uniform thickness. The buckling portion 211 is buckled by hot-caulking. In the present embodiment, the minimum thickness T1 of the caulked portion is the minimum thickness of the caulked fixation portion 21, and the maximum thickness T2 of the buckling portion is the maximum thickness of the caulked fixation portion 21, because the caulked fixation portion 21 has no thick portion as in a prior art.

In the present embodiment, T1 is approximately 0.5 mm, T2 is approximately 1.3 mm, T3 is approximately 1 mm, and L is approximately 3.2 mm. Further, the housing 2 has a body portion 20 immediately under the buckling portion 211, and thickness T4 of the body portion 20 is approximately 1.7 mm. The buckling portion 211 may be tapered, or may have irregularity on the surface thereof.

The gas sensor 1 in the present embodiment is additionally explained below. The gas sensor 1 has a second cover 122, which is fixed to the upper portion of the air side cover 121 by caulking through a water repellent filter 123. The air side cover 121 and the second cover 122 have air conduction holes 125. Likewise, the measurement gas side double cover 111, 112 has gas conduction holes 110. An insulator 13 is disposed in the air side cover 121, and a rubber bush 14 is disposed above the insulator 13.

The detection element 3 is composed of a cup-like solid electrolyte body 31 defining an air chamber 30 inside thereof, and a pair of electrodes respectively provided on the inner and outer surfaces of the solid electrolyte body 31. A pole heater 35 is inserted into the air chamber 30. Output wiring members 193, 194 connected to the electrodes of the detection element 3 are further connected to lead wires 191, 192 in the insulator 13, and taken out of the gas sensor 1 via the rubber bush 14. A wire 195 for supplying electricity to the heater 35 is taken out via the rubber bush 14 as well.

Figure 4A:
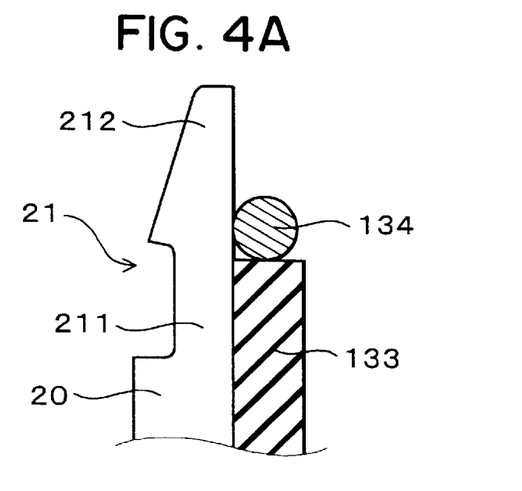
FIGS. 4A to 4C are schematic views showing a process for caulking the caulked fixation portion in the embodiment.
Figure 4B:
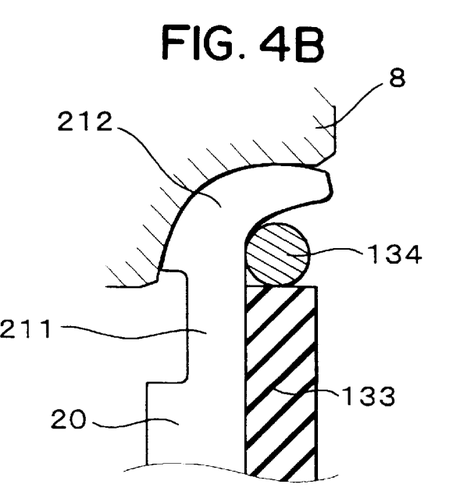

Next, fixation by the caulked fixation portion 21 is explained in more detail. As shown in FIG. 2, first, the detection element 3 is inserted into the insertion hole 29 of the housing 2 through the sealing member 131. Then, the space defined by the detection element 3 in the insertion hole 29 is filled with the powdery sealing material 132. The insulating member 133 is disposed on the sealing material 132, and then the metallic ring 134 is disposed on the insulating member 133. This state is shown in FIG. 4A. As shown in FIG. 4B, successively, a caulking die 8 is brought in contact with the caulked portion 212, and the caulked portion 212 is deformed along the metallic ring 134. Thus, cold-caulking is performed at a room temperature.

Figure 4C:
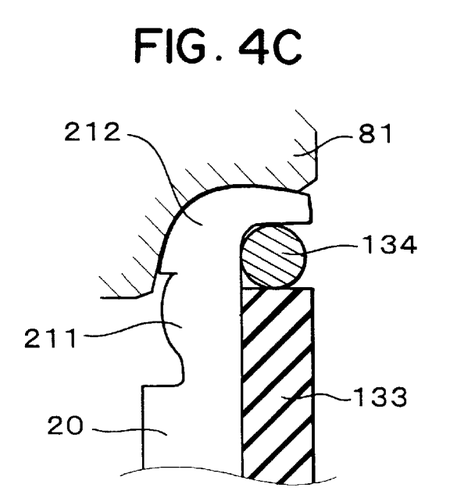

After that, the caulking die 8 is detached, and hot-caulking die 81 is positioned with respect to the caulked fixation portion 21. Electricity is supplied across the hot-caulking die 81 and the housing 2 while applying load thereto. Since the buckling portion 211 is thin, Jule heat is mainly produced at the buckling portion 211, so that the buckling portion 211 is heated and softened to be buckled inwardly in an axial direction, thereby performing caulking fixation. During the caulking fixation, as shown in FIG. 4C, the buckling portion 211 is deformed as if it expands, and is buckled inwardly in the axial direction. As a result, as shown in FIG. 3, the fixation by the caulked fixation portion 21 is realized.

In this case, because the metallic ring 134 has the notch 135, the diameter of the metallic ring 134 is changeable during the caulking fixation. Therefore, the caulked portion 212 can securely contact the metallic ring 134 at an entire circumference thereof by caulking. It is preferable for the caulked portion 212 to directly contact the metallic ring 134. This is because the caulked portion 212 can abut a curved surface of the metallic ring 134 to prevent concentration of stress produced by the caulking force. Incidentally, the air side cover 121 is welded to the outer circumference wall 200 at the fixed position 120, after the caulking fixation is carried out.

Figure 6:
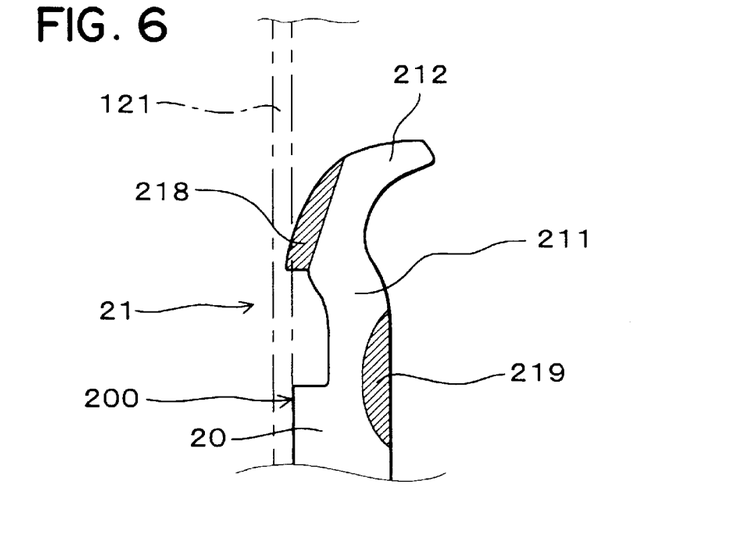
FIG. 6 is an explanatory view for explaining S-like buckling produced at a caulked fixation portion.

Next, samples 1 to 6 having caulked fixation portions with various dimensions were examined whether samples 1 to 6 had S-like buckling portions as shown in FIG. 6. The results are shown in Table 1. Dimensional relationships among T1, T2, T3 in the respective caulked fixation portions of samples 1 to 6 are also shown in Table 1. In Table 1, whether the S-like buckling was produced or not was determined by observation of a cross-section, and dimensions of inner and outer diameters.

FIG. 6 shows a typical S-like buckling of the caulked fixation portion 21 as an example. The S-like bucking is produced by large stresses produced at an outer circumference side 218 of the caulked portion 212 and at an inner circumference side 216 of the bulking portion 211. The large stresses deform the buckling portion 211 inwardly and the caulked portion outwardly in a radial direction of the housing 2. In this case, as shown in FIG. 6, the caulked fixation portion 21 protrudes from the outer circumference wall 200 of the housing 2. The caulked fixation portion 21 having the S-like buckling makes it difficult to fix the air side cover 121 to the housing outer circumference wall 200, or may require an increase in diameter of the air side cover 121.

TABLE 1

| Sample NO. | T1, T2, T3 | T2/T1 | L/{(T1 + T2)/2} | S-like buckling |
|---|---|---|---|---|
| 1 | T1 < T3 < T2 | 1.6 | 3.1 | Produced |
| 2 | | 1.6 | 3.9 | Produced |
| 3 | | 2.0 | 4.0 | Slightly produced |
| 4 | | 2.4 | 3.6 | Not produced |
| 5 | | 3.6 | 3.9 | Not produced |
| 6 | T3 < T1 | 2.4 | 3.6 | Produced |

According to Table 1, in samples 4 and 5 satisfying the conditions of T1<T3<T2, 2<T2/T1, and 3<L/{(T1+T2)/2}, no S-like buckling was produced. In samples 1 to 3 in which 2≧T2/T1, the S-like buckling was produced. Especially, the S-like bucking of sample 1 was prominent. In sample 6 in which T3<T1, S-like buckling was produced as well. Accordingly, it was revealed that the S-like buckling can be prevented by providing the caulked fixation portion 21 satisfying the conditions described above.

Figure 7A:
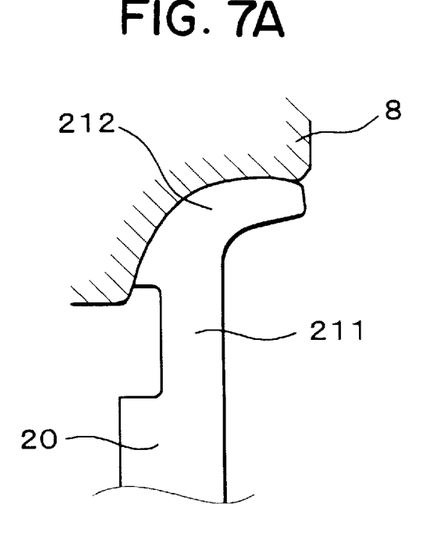
FIGS. 7A and 7B are schematic views for explaining a caulking deficiency of a caulked fixation portion whose dimensions do not satisfy relationships in the embodiment.
Figure 7B:
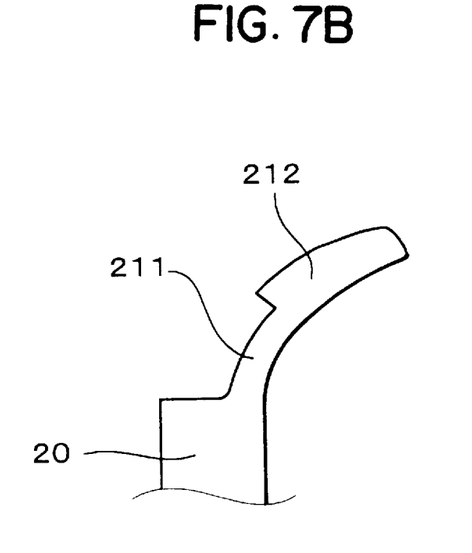

Here, it should be noted if the relation of T1<T3<T2 is not fulfilled, the following problems may occur. First, if T3≧T2, because the bucking portion is not sufficiently thinned comparing to the vicinity thereof, heating of the bulking portion cannot be performed effectively by supplying electricity thereto. This makes it difficult to perform the hot-caulking. Further, if T1≧T3, as shown in FIG. 7B, because the thickness of the buckling portion 211 is smaller that that of the caulked portion 212, strength is decreased as compared to a normally caulked and deformed fixation portion shown in FIG. 7A.

Further, if T2/T1≦2, S-like buckling is produced at the caulked fixation portion, thereby making it difficult to fix the air side cover to the housing outer circumference wall as described above. If L/{(T1+T2)/2}≦3, the caulked portion is too thickened as compared to the length to be smoothly deformed inwardly. The upper limitation of T2/T1 is preferably 6 to prevent the caulked portion from having a too sharpened front end portion to easily perform the cold-caulking. The upper limitation of L/{(T1+T2)/2} is preferably 5 to prevent interference among parts disposed in the housing. The interference is liable to be produced when the length of the caulked portion to be bent inwardly is excessively increased. These dimensions are values before performing the caulking fixation.

Preferable length L of the caulked portion is in a range of approximately 3 to 5 mm. Accordingly, the caulked portion is appropriately caulked. When the length L is less than 3 mm, the caulked portion cannot be sufficiently engaged with an inside part such as the metallic ring, and accordingly, can not securely hold the inside part. When the length L exceeds 5 mm, the length of the caulked portion after caulked is increased to easily interfere with the parts such as the detection element disposed in the gas sensor.

As to the thickness T4 of the housing body portion provided immediately under the buckling portion (see FIG. 1), it is preferable that T3<T4. Accordingly, the buckling portion can be made the thinnest in the housing, so that hot-caulking can be performed to buckle the buckling portion effectively. If T3≧T4, it is difficult for the buckling portion to be heated by electricity supplied thereto. More preferably, the thickness T4 satisfies a relationship of T3<T2<T4. Accordingly, the cover can be fixed to the outer circumference wall of the housing body portion having T4 without causing interference with the caulked portion.

That is, according to the present embodiment, the caulked fixation portion 21 satisfies the above dimensional relationships, and the caulked portion 212 and the buckling portion 211 has no thick portion therebetween. The size of the gas sensor 1 and the weight of the housing 2 can be reduced, because the gas sensor 1 has no thick portion between the caulked portion 212 and the buckling portion 211.

Accordingly, material cost of the housing 2 can be reduced. Further, as shown in Table 1, because the S-like buckling as shown in FIG. 6 is not produced to the caulked fixation portion 21 satisfying the above dimensional relationships, the air side cover 121 can be securely fixed to the outer circumference wall 200 of the housing 2. This contributes to the size reduction of the gas sensor 1.

While the present invention has been shown and described with reference to the foregoing preferred embodiment, it will be apparent to those skilled in the art that changes in form and detail may be made therein without departing from the scope of the invention as defined in the appended claims.

For example, the shape of the detection element is not limited to the cup-like shape as in the present embodiment, but may be a lamination type. It is apparent the present invention can be applied to various sensors such as CO sensors, $NO_x$ sensors, and gas sensors such as HC, in addition to oxygen sensors as described in the present embodiment.

What is claimed is:

1. A gas sensor comprising:
   a detection element;
   a cylindrical housing having an insertion hole for receiving the detection element therein;
   a measurement gas side cover covering a first end portion of the housing in an axial direction of the housing;
   an air side cover covering a second end portion of the housing in the axial direction;
   a caulk fixation portion integral with the second end portion of the housing, for fixing the detection element in the insertion hole by caulking; and
   a sealing member interposed between the caulk fixation portion and the detection element;
   wherein the caulk fixation portion has a force applying portion for imparting a caulking force to the sealing member directly, a body portion having a thickness larger than the force applying portion in a radial direction of the housing, and a buckling portion provided between the force applying portion and the body portion for increasing the caulking force by buckling in the axial direction; and
   wherein the caulk fixation portion before caulking satisfies dimensional relationships of:

$T1<T3<T2$;

$2<T2/T1$;

and $$3 < L / \{(T1+T2)/2\},$$

in which T1 is a minimum thickness of the force applying portion in the radial direction of the housing, T2 is a maximum thickness of the force applying portion in the radial direction, T3 is an average thickness of the buckling portion in the radial direction, and L is a length of the force applying portion in the axial direction.

2. The gas sensor of claim 1, wherein the sealing member is a metallic ring.

3. The gas sensor of claim 2, wherein the metallic ring has a notch.

4. The gas sensor of claim 2, wherein:
the metallic ring generally has a circular cross-sectional shape; and
the force applying portion directly abuts the metallic ring by caulking.

5. The gas sensor of claim 1, wherein:
the force applying portion has the minimum thickness T1 at a front end thereof and has the maximum thickness T2 at an end of a side of the buckling portion; and
the buckling portion is buckled by hot-caulking.

6. The gas sensor of claim 1, wherein:
the force applying portion has a sloped outer wall from a first end portion having a thickness T2 at a buckling portion side to a second end portion having the thickness T1 at a front end thereof; and
the first end portion of the force applying portion is directly and integrally connected to the buckling portion to form a step, the buckling portion having a thickness, which is inevitably smaller than the thickness T2 and has the average thickness T3.

7. The gas sensor of claim 1, wherein a maximum thickness of the caulk fixation portion is the maximum thickness T2 of the force applying portion.

8. The gas sensor of claim 7, wherein the force applying portion has a thickness, which is continuously increased from a front end thereof having a minimum thickness T1 to a buckling portion side end thereof having a maximum thickness T2.

9. The gas sensor according to claim 1, wherein the body portion having a flat outer surface connected to an inner surface of the air side cover, and the buckling portion being provided at a recess portion between the force applying portion and the body portion hand having a an outer surface expanding radially outward.

10. The gas sensor according to claim 9, wherein the flat outer surface of the body portion contacts the inner surface of the air side cover.

11. A method of fabricating a gas sensor comprising:
inserting a detection element into an insertion hole of a cylinderical housing, the insertion hole being open at a first end portion of the housing;
disposing a sealing member in a space formed by the detection element in the insertion hole;
caulking a caulk fixation portion integrally provided with the first end portion of the housing and including a first portion at a front end thereof and a buckling portion disposed between the first portion and the housing so that the first portion is deformed along the sealing member at a room temperature; and
caulking the caulk fixation portion while heating the caulk fixation portion so that the buckling portion is buckled, wherein the caulk fixation portion before caulking at room temperature satisfies dimensional relationships of:

$$T1 < T3 < T2;$$

$$2 < T2/T1;$$

and $$3 < L / \{(T1+T2)/2\},$$

in which T1 is a minimum thickness of the caulk fixation portion in the radial direction of the housing, T2 is a maximum thickness of the caulk fixation portion in the radial direction, T3 is an average thickness of the buckling portion in the radial direction, and L is a length of the first portion in the axial direction.

12. The method of claim 11, wherein the first portion has a thickness, which is continuously increased from a front end thereof having a minimum thickness T1 to a buckling portion side end thereof having a maximum thickness T2; and
the buckling portion side end of the first portion is directly connected to the buckling portion to form a step.

13. A cylindrical housing for a gas sensor, having an insertion hole for holding a detection element of the gas sensor, the cylindrical housing comprising:
a caulk fixation portion to be caulked for fixing the detection element in the insertion hole through a sealing member, the caulk fixation portion including:
a force applying portion provided at a front end in an axial direction of the housing for imparting a caulking force to the sealing member directly; and
a buckling portion provided at an opposite side of the force applying portion with respect to the axial front end, for increasing the caulking force by buckling in the axial direction, wherein:
the caulk fixation portion satisfies dimensional relationships of:

$$T1 < T3 < T2;$$

$$2 < T2/T1;$$

and $$3 < L / \{(T1+T2)/2\},$$

in which T1 is a minimum thickness of the force applying portion in the radial direction of the housing, T2 is a maximum thickness of the force applying portion in the radial direction, T3 is an average thickness of the buckling portion in the radial direction, and L is a length of the force applying portion in the axial direction.

14. The cylindrical housing of claim 13, wherein:
the caulk fixation portion has the minimum thickness T1 at a front end thereof and has the maximum thickness T2 at an end of a side of the buckling portion; and
the buckling portion has an approximately uniform thickness.

15. The cylindrical housing of claim 13, wherein the force applying portion is tapered from the side of the buckling portion toward the front end thereof.

16. The cylindrical housing of claim 13, wherein:
the caulk fixation portion further has a body portion at an opposite side of the buckling portion with respect to the force applying portion; and
the buckling portion is stepped from the force applying portion and the body portion.

* * * * *